United States Patent [19]

Rosenblum et al.

[11] Patent Number: 5,124,464
[45] Date of Patent: Jun. 23, 1992

[54] METHOD OF PREPARING METALLOCENE COMPOUNDS

[75] Inventors: Myron Rosenblum, Lexington, Mass.; Stephen A. Matchett, Lisle, Ill.

[73] Assignee: Brandeis University, Waltham, Mass.

[21] Appl. No.: 366,605

[22] Filed: Jun. 15, 1989

Related U.S. Application Data

[62] Division of Ser. No. 138,359, Dec. 28, 1987.

[51] Int. Cl.$^5$ .................... C07C 15/12; C07F 17/00
[52] U.S. Cl. ............................. 556/138; 556/143; 528/9; 528/395; 585/24; 585/25; 585/26
[58] Field of Search ............. 528/9, 395; 585/24, 585/25, 26; 556/138, 143

Primary Examiner—Joseph L. Schofer
Assistant Examiner—Fred Zitomer
Attorney, Agent, or Firm—Hamilton, Brook, Smith & Reynolds

[57] ABSTRACT

This invention describes a novel method of preparing metallocene compounds. The invention is based on synthesis of novel bis cyclopentadienides that, under appropriate conditions, will either encapsulate a transition metal to produce a metallocene such as ferrocene, or ferrocene derivative, or will yield a polymeric metallocene. Compounds produced by this process are useful as catalysts in propulsion systems, or as anti-knock compounds in gasolines.

10 Claims, 2 Drawing Sheets

METHOD OF PREPARING METALLOCENE COMPOUNDS

GOVERNMENT SUPPORT

The United States Government has certain rights in this invention pursuant to a grant provided by the Department of Energy.

This application is a division of application Ser. No. 07/138,359 Dec. 28, 1987.

BACKGROUND

The synthesis of the organometallic compound ferrocene in the early nineteen fifties has sparked great interest in construction and use of these compounds. This is especially so in terms of synthesis and properties of stacked columns of organometallics. See also Werner, *ANG. CHEMIE INT. ED.* 16, 1–64 (1977); Lee, M.-T., et al., *Organo*-metallics 3, 539–547 (1985).

Some of the monomeric and polymeric organo-metallics possess unusual properties useful in electrical conduction or catalysis. For example, ferrocene ($R^1MR^1$) where $R^1$ = the cyclopentadienyl ring and M = Fe, and ferrocene polymers have been used as anti-knock agents in gasolines, as combustions catalysts in rocket propellants, and as reversible electronic conductors. See U.S. Pat. No. 3,968,126 (1976) (combustion catalyst in rocket propellants); U.S. Pat. No. 4,025,541 (1977) (electrical conducting compounds); U.S. Pat. No. 3,807,213 (binder compositions for rocket propellants).

Ferrocene itself was first prepared utilizing the reaction of cyclopentadienylmagnesium bromide with $FeCl_3$ in diethyl ether-benzene solution.

Recent synthetic methods of producing other organometallic compounds rely on the use of metal-promoted coupling reactions of organic halides with organometallic derivatives. See E. Negishi, *PURE APPL. CHEM.* 53, 2333 (1981); D. Milstein and J. K. Stille, *H. AM. CHEM. SOC.* 101, 4981 (1979); Felkin, H. and G. Swierczewski, *TETRAHEDRON* 31, 2735-2748 (1975); Tamao, K. et al., *BULL. CHEM. SOC. JAPAN* 49, 1958–(1969). This includes the synthesis of metallocenes by the coupling of metallated ferrocenes with haloaromatics. Lee, M. T. et al., *Organometallics* 3, 539 (1985). In this latter procedure, however, the polymers can only be derived from monomeric metallocenes capable of being converted into their dichlorozinc derivatives, as exemplified by the following reaction.

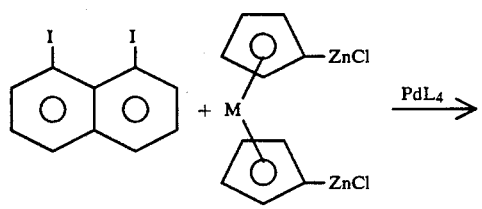

-continued

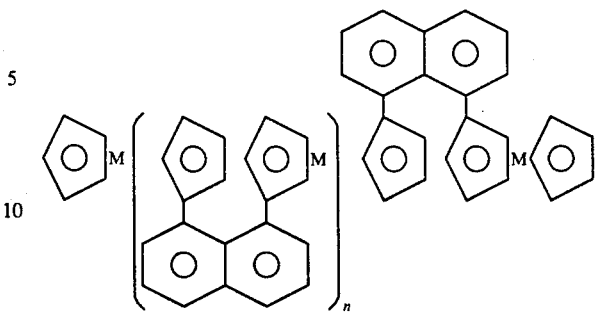

Moreover, attempts to prepare polymers from certain dianionic cyclopentadienides derived from as and S-indacenes, fulvalene, bis(cyclopentadienyl)-methane and pentalene have generally failed. See Bell, W. L. et al., *ORGANOMETALLICS,* 6, 266 (1987); Katz, T. J. et al., *J. AM. CHEM. SOC.,* 94, 3281, 6204 (1972), and *J. Am. Chem.* 95, 2934 (1973); Katz, T. J. and J. Pesti, *J. Am. Chem. Soc.,* 104, 346 (1982). This is likely due to entropic factors, which favor dimer or trimer formation over chain growth polymerization processes.

SUMMARY

The present invention relates to a novel method of synthesizing organometallic compounds. In particular, the invention describes a method of synthesizing monomeric and polymeric organometallic units that are attached to a hydrocarbon skeleton. The method is of general utility in the synthesis of such substituted compounds and can be used to create polymers represented by the formula,

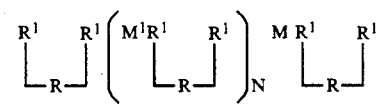

where $R^1$ represents a cyclopentadienyl ligand, R represents a disubstituted aromatic residue, M and $M^1$ can be any divalent transition metal and N is a positive number greater than 1. The metal M can be the same as metal $M^1$ or M and $M^1$ can be different metals selected individually from the group of transition metals.

This invention is based on the preparation of novel bis-cyclopentadienides in which the cyclopentadiene rings carry a negative charge. Furthermore, the cyclopentadienides embodied in this invention can be used to create substituted monomeric compounds in which the metal moiety is encapsulated between adjacent cyclopentadienyl rings (e.g., ferrocene and ferrocene derivatives).

The invention also includes the structure and synthesis of a novel compound useful in production of said compounds, 1,8 bis(cyclopentadienyl)-naphthalene. This compound is only one of a general series of related biscyclopentadienyl aromatics used in embodiments of this invention.

Because this invention makes it unnecessary to create metallated derivatives of metallocenes during synthesis of metallocene polymers, the syntheses described herein are useful in producing such stacked polymers simpler and more efficiently. These stacked organometallic polymers can find use as reversible electronic conductors in batteries. Moreover, specific ferrocene and ferrocene derivatives are useful in a wide variety of catalytic applications and as anti-knock components of gasolines.

DESCRIPTION OF THE INVENTION

Figure 1:
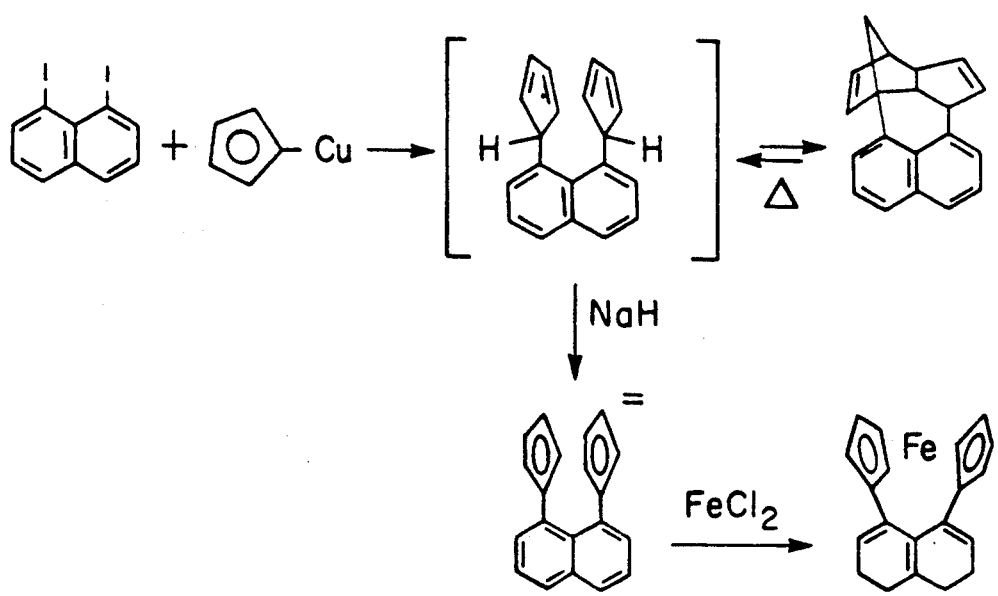
FIG. 1 represents the chemical structures of the synthetic pathway for producing 1,8 bis(cyclopentadienyl)-naphthalene, its dianion, and the resultant encapsulated metallocene, 1,8 diferro-cenylnaphthalene (1,1'-[1,8 naphthylidene]ferrocene).

The present invention relates to novel methods of making substituted organometallic compounds of two general types, represented as follows:

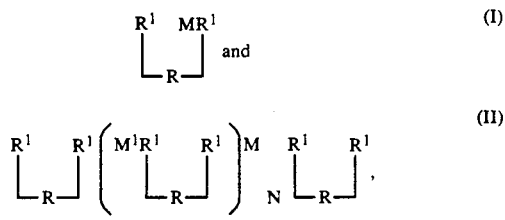

where $R^1$ is the cyclopentadienyl ligand, R is a disubstituted aromatic compound, M and $M^1$ is a divalent cationic metal and N is an integer greater than 1. As used herein, "polymeric" metallocenes or "polymeric" organometallic compounds are defined as those compounds having formula type II. As used herein, the term "metallocene" means metal-aromatic sandwich compounds of general formulae type I and type II. Metallocenes can also include ferrocene ($R^1MR^1$, where $R^1$ is the cyclopentadienyl ligand; M=FE).

Other metals can replace iron as the metal moiety in this invention. In such compounds, M and $M^1$ can be selected from metals both to the left and right of iron in the Periodic Table. For example, metallocenes embodied in this invention are those whose metals include, but are not limited to, iron, ruthenium, osmium, nickel, molybdenum, vanadium, rhenium or technetium. Both M and $M^1$ may be the same metal or, in some embodiments of this invention M and $M^1$ are different metals selected individually from the group consisting of divalent transition metals.

Synthesis of type I and II compounds described herein yields organometallic sandwich compounds that are held on a hydrocarbon framework. This is accomplished by using as starting materials, dihalogenated aromatic compounds that can contain peri-substitutions of halogens, or halogen groups that are 1,4-disposed with respect to one another on the aromatic ring. For example, formation of substituted metallocenes of type II embodied in this invention can be accomplished using 9,10 dihaloanthracene, 1,4 dihalobenzene and 4,4'dihalobiphenyl as the hydrocarbon unit.

In particular embodiments of this invention, synthesis of metallocenes with a hydrocarbon framework consists of coupling 1,8 diiodonaphthalene to a pair of cyclopentadienyl ligands. In preferred embodiments of this invention, cyclopentadiene is lithiated and 1,8 diiodonaphthalene is added to the cyclopentadienyllithium in the presence of copper bromide-dimethylsulfide.

The methods described herein are based on a series of related novel compounds, the bis-(cyclopentadienyl)-cycloaromatics. In particular, this is exemplified by the above-mentioned 1,8-bis(cyclopentadienyl)naphthalene.

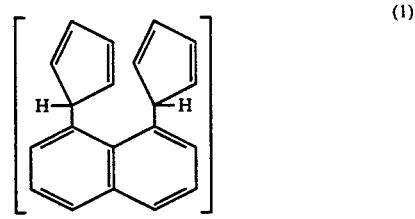

The bis(cyclopentadienyl) cycloaromatics of the present invention exist in the form of their Diels-Alder adducts, as exemplified by:

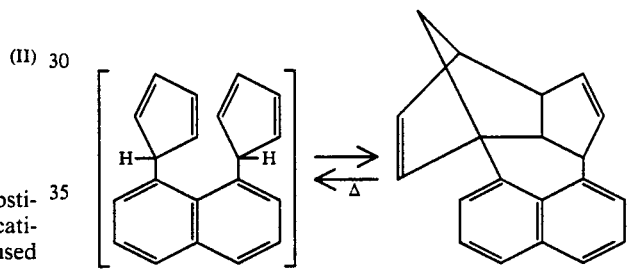

The classical Diels-Alder reaction involves the 1,4 addition of a double bond (the dienophile) to a conjugated diene. The reaction is easy and rapid and of very broad scope. As exemplified in this invention, aromatic compounds may also behave as dienes. Benzene and naphthalene, however, are quite resistant to forming Diels-Alder adducts. It is for this reason that the hydrocarbon framework of compounds disclosed in this invention do not themselves participate in the Diels-Alder addition reactions.

The reverse Diels-Alder reaction is also exceedingly useful since no catalyst is needed for the reaction. See Kwart and King, CHEM. REV. 68, 415-447 (1968). In the presence of a strong base, the intermediate bis(diene) compound such as (1) can be converted to the dianionic bisdienide as exemplified by

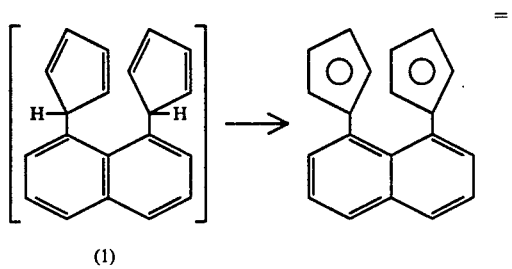

The strong base may be selected from the group consisting of sodium hydride, n-Butylithium, lithium diisopropylamide, trityllithium. In preferred embodiments of this invention, the base is sodium hydride (NaH).

The resulting dianionic compound is able to "encapsulate" or capture a dicationic metal without need of catalyst to form a substituted metallocene of type I.

Formation of the Diels-Alder adduct, the corresponding dianion, and the use of the dianion to produce a substituted "type I" ferrocene is illustrated in FIG. 1 for the compound 1,1'-[1,8 naphthylidene 1,8 diferrocenylnaphthalene. As described herein, M can be any transition metal.

In preferred embodiments of this invention, the formation of a cyclopentadienylaromatic complex and its resultant dianion can be conveniently performed in an organic solvent such as decalin. Other solvents useful in this regard can be selected from the group consisting of toluene, xylene and mesitylene.

Further embodiments of this invention concern use of these cyclopentadienides to create type II polymers.

Figure 2:
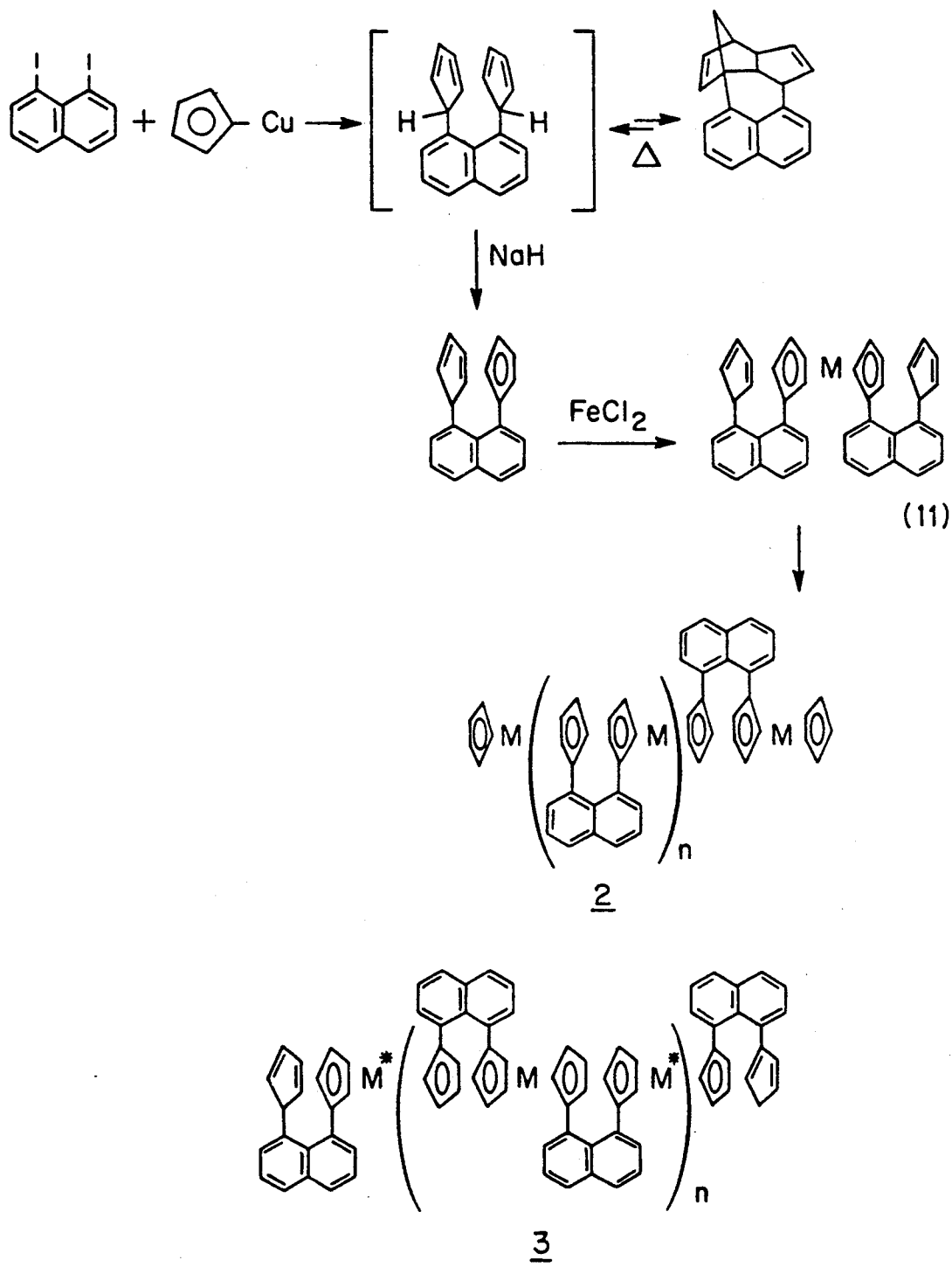
FIG. 2 represents the chemical structures of the synthetic pathway leading to production of the monoanionic form of 1,8 bis(cyclopentadienyl)-naphthalene; subsequent quenching with a divalent metal to yield the dimer (11) and treatment of the dimer with strong base and a metal salt to yield the type II polymer (2). Treatment of compound (11) with strong base and different metals (M and M*) can yield the herometallic type II polymer (3).

The problems associated with the inability to form polymers can be solved by treating a bis-(cyclopentadienide), such as 1,8 biscyclopentadienyl naphthalene, with 1 molar equivalent of strong base to form the monoanion (FIG. 2).

The method of encapsulating the metal, as in the formation of type I compounds, can be bypassed in the following manner. Molecular mechanics calculations show large distortions in the naphthalene ring system in the dianionic compound 1,8 dicyclopentadienide (FIG. 1) and a difference in steric energy of 6.5 Kcal/mole between this dianion and the diradical derived from it. Such effects should make it possible to prepare the monoanion either by treatment of the diene (1) with a base of suitable strength, or more conveniently, by carrying out the deprotonation of the diene (1) with one molar equivalent of strong base. In preferred embodiments of this invention the strong base is NaH and the deprotonation reaction can be carried out in toluene at approximately 110°–115° C. for about one hour. Weaker bases can also be used in excess, such as potassium t-butoxide. Quenching with a divalent metal can yield the dimer 11 (FIG. 2). This compound, on further transformation to its anionic bis-cyclopentadienide and treatment with metal salt, can yield a type II polymer (compound 2), as sum-marized in FIG. 2. Subsequent transformations of the dimeric form (exemplified by 11) to yield stacked polymers (2) do not require as stringent conditions as does formation of the monoanion or dimer itself. For example, the dimer can be treated with either NaH or n-butyllithium and treated with metal salt at approximately room temperature. Using these methods, it can be possible to prepare hetero-metallic polymers in which a metal center of the unit 11 alternates with a second metal center [M*]joining these units, as in compound 3 of FIG. 2.

These methods, based on essentially ionic reactions between a cationic metal and negatively charged cyclopentadienyl ring, avoid the need to convert monomeric units into their dichlorozinc derivatives prior to polymerization.

The invention is illustrated further by the following Examples.

EXAMPLE I

SYNTHESIS OF 1,8 DICYCLOPENTADIENYL NAPHTHALENE

This Example illustrates synthesis of one form of cyclopentadienyl Diels-Alder adduct. Freshly cracked cyclopentadiene (0.2 mL, 2.4 mMoles) was lithiated with one equivalent (1.5 mL of a 1.6 M solution in hexane, 2.4 mMoles) of n-butyl lithium in 10 mL of distilled THF at room temperature. This procedure produced a white precipitate which was dissolved with several additional mLs of THF. The resulting homogeneous solution was very pale yellow after several minutes but was allowed to stir for 0.5h prior to use.

Using a 100 mL Schlenk flask (fitted with a Claisen adaptor and an addition funnel), 0.493 g (2.4 mMoles) of $CuBr-SMe_2$ complex was suspended in 10 mL of distilled THF and cooled to about −50° C. The lithiated cyclopentadiene solution was then loaded into the addition funnel and allowed to drip into the suspension of $CuBr-SMe_2$ over the course of about 0.75h.

At this point, the temperature was increased to approximately −20° C. and the system allowed to equilibrate (approximately 1h). The resulting solution was yellow and homogeneous.

In a separate flask, 0.339 g (0.878 mMoles) of 1,8 diiodonaphthalene was dissolved in 6 mL of THF. This was slowly added through the side arm of the Claisen adaptor (syringe pump or multiple 1 mL injections over the course of 1h) to prevent metal halogen exchange with any residual lithiated cyclopentadiene in the addition funnel. The resulting yellow/orange solution was stirred overnight at about −20° C. continuing to darken in color to a red homogeneous solution.

Reaction was monitored by silica TLC using hexane as the eluting solvent. The product is a slightly fluorescent spot with an $R_f=0.34$.

The reaction was then quenched by pouring it into about 50 mL of a saturated $NH_4Cl$, separating the organic phase, drying on $MgSO_4$ and evaporation of the solvent. The resulting residue was extracted with 100–120 mL of hexane which upon evaporation gave 0.122 g of crude product as a white solid mixed with a yellow oil.

The product was purified by flash chromatography (6"silica, 50 mm column, hexane, 50 mL aliquots) to give 0.064 g of the product (28.5% isolated yield).

EXAMPLE II

FORMATION AND USE OF THE BISCYCLOPENTA-DIENYLNAPHTHALENE TO FORM AN

ENCAPSULATED 1,8 FERROCENYLNAPHTHALENE

The deprotonation-retro Diels-Alder reaction of 1,8 dicyclopentadienyl naphthalene was performed in decalin, prepared in the following manner. The decalin was treated with concentrated sulfuric acid for several hours and was then washed with water, $Na_2CO_3$ additional water and dried on $CaSO_4$. The resulting clear liquid was fractionally distilled to yield purified decalin.

NaH (1.435 g of a 57% mixture in oil = 0.818 g reagent, 34 mMoles) was washed under argon with 2×20 mL aliquots of hexane to remove the mineral oil and leave a grey powder. This was combined in a 25 mL roundbottom flask (fitted with a reflux condensor and a gas inlet) with 1,8 dicyclopentadienylnaphthalene (0.040 g, 0.16 mMoles) and suspended in 5 mL of decaline. The suspension was brought to reflux (190° C.) for 20h.

The suspension was then treated with 0.203 g (1.6 mMoles) of anhydrous FeCl$_2$. At this point 3 mL of THF were added to aid the solubility and hence the reactivity of the dianion. This mixture was allowed to stir overnight. The reaction was then worked up by carefully treating the reaction mixture with dilute aqueous HCl and dried on MgSO$_4$. The THF was removed on the rotovap, leaving a yellow decaline solution from which yellow crystals of the product 1, 1'[1,8 naphthylidene] ferracene, grew. The crystals were isolated by filtration to give 0.011 g (22% isolate yield) of the product. $^1$Hnmr: (CDCl$_3$, ppm) 7.88 (d, 2H), 7.60 (d, 7.2 hz, 2H), 7.42 (t, 7.5 Hz, 2H), 4.28 ("t", 1.5 Hz, 4H), 4.23 ("t", 1.5 Hz, 4H). $^{13}$Cnmr (CDCL$_3$, ppm) 131.4, 130.89, 128.82, 124.17, 71.38, 70.02.

As described herein, the invention is useful in synthesis of metallocenes that contain a non-interacting hydrocarbon framework. These metallocenes can be used as anti-knock compounds in gasolines, or as catalysts in propulsion systems. The method avoids the need for dichlorozinc derivatives and catalysts, and is generally applicable to a wide variety of transition metals.

EQUIVALENTS

Those skilled in the art will recognize, or be able to ascertain, with no more than routine experimentation, many equivalents to the specific embodiments of the invention described herein. These equivalents are intended to be encompassed by the following claims.

We claim:

1. A method of making metallocene compounds encapsulating divalent metals comprising:
   a. reacting a lithiated cyclopentadiene in the presence of a copper halide-dimethylsulfide complex with an aromatic compound dihalogenated at either alternate or peri-positions, wherein the halogen is selected from the group consisting of chlorine, bromine, iodine and astatine; and
   b. reacting the resultant cyclopentadienyl-substituted aromatic compound with a divalent transition metal salt, wherein said transition metal includes the lanthanides and actinides.

2. A method of claim 1, wherein the dihalogenated aromatic compound is 1,8 dihalonaphthalene.

3. A method of claim 2, wherein the halogen is selected from the group consisting of iodine, chlorine and bromine.

4. A method of claim 1, wherein the metal moiety of the divalent transition metal salt is a transition metal other than a lanthanide or actinide.

5. A method of preparing 1, 1' -(1,8 naphthylidene) metallocene, comprising the steps of:
   a. reacting lithiated-cyclopentadiene with 1,8 dihalonaphthalene in the presence of a copper dimethylsulfide complex, wherein the halogen is selected from the group consisting of chlorine, bromine, iodine and astatine;
   b. reacting the resultant compound with strong base;
   c. refluxing the resultant suspension and treating it with an anhydrous divalent transition metal salt, wherein said transition metal includes the lanthanides and actinides; and
   d. drying and crystallizing the product.

6. A method of claim 5, wherein the dimethylsulfide complex is a copper bromide dimethylsulfide complex and the strong base is sodium hydride.

7. A method of claim 5, wherein the anhydrous divalent transition metal salt contains any transition metal moiety other than a lanthanide or actinide.

8. A method of preparing 1,1' -(1,8 naphthylidene) ferrocene, comprising the steps of:
   a. reacting a lithiated cyclopentadiene with 1,8 diiodonaphthalene in the presence of a copper bromide-dimethylsulfide complex at about minus 20° C. for about 12 hours;
   b. refluxing the resulting compound with sodium hydride at about 190° C. for about 20 hours;
   c. treating the suspension with anhydrous Fe (II) chloride; and
   isolating the product, 1, 1' -(1,8 naphthylidene) ferrocene, by reaction with dilute aqueous HCl, drying on MgSO$_4$ and filtration.

9. Encapsulated metallocenes produced according to the process of claim 1 and having the formula

where R$^1$ is the cyclopentadienyl ligand, M is a divalent cationic transition metal, wherein said transition metal includes the lanthanides and actinides, and R is an aromatic compound disubstituted at either alternate or peri- positions.

10. Metallocenes of claim 9, wherein M is any divalent transition metal other than a lanthanide or actinide, and R is from a dihalonapthalene, wherein the halogen is selected from the group consisting of chlorine, bromine, iodine and astatine.

* * * * *